United States Patent [19]

Matsumori

[11] Patent Number: 5,521,185
[45] Date of Patent: May 28, 1996

[54] METHODS FOR INHIBITING GRAFT REJECTION AND IL-1 PRODUCTION

[75] Inventor: Akira Matsumori, 16-22, Segawa 5-chome, Mino-shi, Osaka 562, Japan

[73] Assignees: Otsuka Pharmaceutical Co., Ltd., Tokyo; Akira Matsumori, Osaka, both of Japan

[21] Appl. No.: 331,615

[22] PCT Filed: Feb. 28, 1994

[86] PCT No.: PCT/JP94/00326

§ 371 Date: Nov. 2, 1994

§ 102(e) Date: Nov. 2, 1994

[87] PCT Pub. No.: WO94/21836

PCT Pub. Date: Sep. 29, 1994

[30] Foreign Application Priority Data

Mar. 2, 1993 [JP] Japan .................................. 5-041227
Mar. 2, 1993 [JP] Japan .................................. 5-41227

[51] Int. Cl.$^6$ .......................... A61K 31/495; A61K 31/47
[52] U.S. Cl. .......................... 514/252; 514/254; 514/312
[58] Field of Search .................................. 514/252, 254, 514/312

[56] References Cited

U.S. PATENT DOCUMENTS 4,415,572  11/1983  Tominaga et al. .................. 514/252

FOREIGN PATENT DOCUMENTS 0552373  7/1993  European Pat. Off. .
0623598  11/1994  European Pat. Off. .
57-77676  5/1982  Japan .
62-135423  6/1987  Japan .
58-83677  5/1994  Japan .

OTHER PUBLICATIONS

Busch et al, "The Inhibitory Effects of a Positive Inotropic Quinolinone Derivative, 3,4-dihydro-6-[4-(3,4-dimethoxybenzoyl)-1-piperazinyl]-2-(1H)-Quinolinone(OPC-8212), on Bone-Marrow Progenitor Cells and Peripheral Lymphocytes", Eur. J. Clin. Pharmacol., 42:629–634 (1992).

JPA 57-77676 (Otsuka Pharmaceutical Co., Ltd.) May 15, 1982—Derwent Abstract.

JPA 58-83677 (Otsuka Pharmaceutical Co., Ltd.) May 19, 1983—Derwent Abstract.

JPA 62-135423 (Otsuka Pharmaceutical Co., Ltd.) Jun. 18, 1987–Derwent Abstract.

Primary Examiner—Marianne M. Cintins
Assistant Examiner—Kevin E. Weddington
Attorney, Agent, or Firm—Sughrue, Mion, Zinn, Macpeak & Seas

[57] ABSTRACT

This invention provides a method of inhibiting graft rejection comprising administering a carbostyril derivative and/or its salt to a subject in need of such treatment. The method of this invention enhances the graft survival rate and can be advantageously used in the transplantation of various organs and tissues. This invention also relates to a method for inhibiting IL-1 production comprising administering a carbostyril derivative and/or its salt to a subject in need of such treatment. This method is effective in the prevention and treatment of diseases arising from excess IL-1 production, such as inflammatory diseases, osteoporosis, myelocytic leukemia, etc.

4 Claims, 5 Drawing Sheets

METHODS FOR INHIBITING GRAFT REJECTION AND IL-1 PRODUCTION

This application is a 371 of PCT/JP94/00326, filed Feb. 28, 1994.

TECHNICAL FIELD

This invention relates to a graft rejection inhibitor and an IL-1 production inhibitor, each comprising a defined carbostyril derivative as an active ingredient.

BACKGROUND ART

The organ transplantation performed these days encompasses a broad spectrum of tissues, including cardiac, pulmonary, hepatic, pancreatic, small intestinal, renal, corneal, dermal, combined heart-lung and bone marrow transplants. Meanwhile, as drugs essential to such organ transplantations, immunosuppressants such as cyclosporine, azathioprine, mizoribine, OKT3 which is a monoclonal antibody, steroids, antilymphocyte globulins, etc. are in use for prophylactic or therapeutic immunosuppression in such organ transplantations. The advent of these drugs resulted in a marked enhancement of the success rate of transplantation but the massive and prolonged administration of the drugs met with not only severe myelosuppression and the consequent side effects such as leukopenia, thrombopenia, anemia and renal failure due to nephrotoxicity but also the risk of dangerous complications such as increased susceptibility to infection, anemia, bleeding tendency and so on. Therefore, the dosage of such drugs has to be restricted in many cases.

In recent years, for further enhancement of the success rate of transplantation and for the purpose of alleviating side effects, research and development efforts are being made on FK506, RS61443, 15-deoxyspergualin; DSG), adhesion molecule antibodies, etc., but antibody preparations have the disadvantage of being unsuited for maintenance therapy requiring long-term administration because heterologous proteins are injected. Moreover, although combination therapies using the above-mentioned drugs are practiced in GVHD (graft-versus-host disease), a unique disease complicating a homoplastic marrow transplantation, the therapeutic effects have not necessarily been satisfactory. Therefore, the industry needs research and development for a new drug which may be termed a graft rejection inhibitor and can be used in a long-term-maintenance therapy for positive suppression of both acute and chronic rejections with a reduced risk of side effects in cases of the organ transplantations mentioned above.

Meanwhile, a large number of cytokines has been discovered as proteineous factors which inhibit the expression of various physiologic functions such as immune response, inflammatory reaction and hematopoiesis in the host and with the progressive elucidation of their structures and actions, it has become increasing clear that the actions of these cytokines are not only confined to the immune system but extend to various biologic functions, thus being closely associated with the genesis, differentiation, homeostasis and pathophysiology of the body.

Among said cytokines, IL-1 is a proteinaceous factor produced chiefly from monocytes and macrophages and is a polypeptide with a molecular weight of about 12000–18000 [S. B. Mizel et. al., Immunol. Rev., 63, 51–71, 1982]. This IL-1 acts on various kinds of cells, exhibits various biological activities and, hence, plays an important role in nearly all the vital reactions, such as immunity, inflammation, hemato- poiesis, endocrine system and cerebral nervous system. IL-1 occurs in two distinct molecular forms as classified by isoelectric point, viz. pI5 and pI7, and whereas the former is known as IL-1α, the latter is known as IL-i1β Oppenheim, J. J., et al., Immunol. Today, 7, 45, 1986: Dinarello, C. A., Adv. Immuno., 44, 153, 1988]. The homology of the amino acid sequence of the respective molecular forms is as high as 60–70% even among different animal species but the two molecular forms show only a low homology of 25% even in the same species. Moreover, both IL-1α and IL-1β reportedly bind to the same receptor on the cell membrane [Lowenthal, K., et al., J. Exp. Med., 164, 1060, 1986]. It has also been reported that IL-1 exerts direct growth inhibiting and cytocidal actions on various tumor cells [Onozaki, K., et al., J. Immunol., 135, 3962, 1985], thus producing antitumoral effects [Nakamura, S., et al., Jpn. J. Cancer Res., 77, 767, 1986: North, R. J., et al., J. Exp. Med., 168, 2031, 1988]. In addition, with regard to this IL-1, not only the above-mentioned antitumor effect, such other effects have been reported as fever induction, synovial cell proliferation, cartilage destruction, bone destruction, promotion of bone resorption, impairment of vascular endothelial cells, stimulation of mesangial cell proliferation, induction of prostaglandin $E_2$ ($PGE_2$) production, inhibition of development of fertilized ova, induction of $PGE_2$ and PGE2α production, promotion of granulation, promotion of IL-1-associated autocrine leukemic cell proliferation, IL-1-related inflammation locally induced by crystalline urea, and, as effects on the immune system, stimulation of the differentiation and augmentation of activity of T, B and NK cells, induction of PGE production, induction of production of cytokines such as IL-2, IL-6, TNF, GM-CSF, G-CSF, etc., induction of NGF from fibroblasts, induction of sleep, hyperalgia and anorexia, induction of ACTH production, and an action to increase glucocorticoids [Onozaki, K., Biomedicine & Therapeutics, 24 (1), 27–31, 1990].

Though, as described above, IL-1 plays a critical role in the inhibition of biologic functions such as the expression of immune response, inflammatory reactions and hematopoiesis, an excess production of IL-1 in the body may cause various diseases accompanied by inflammation. Moreover, in view of the biological activities of IL-1, its excess production in vivo may trigger the onset of serious diseases such as rheumatoid arthritis, Lyme disease, osteoporosis, Kawasaki disease, poisoning-shock syndrome, gout, glomerulonephritis, endometritis, premature delivery, abortion, granuloma, acute myelocytic leukemia and so on. For the prevention and treatment of such diseases, drugs capable of inhibiting an excess production of IL-1 in vivo should be effective but no drug possessed of such an action has been developed. Therefore, a keen demand exists for new drug research and development in this segment of the industry.

DISCLOSURE OF INVENTION

It is, therefore, an object of this invention to provide a novel graft rejection inhibitor that would meet the industry's demand mentioned above and particularly a novel graft rejection inhibitor that would contribute to a further prolongation of graft survival in cardiac transplantation.

It is a further object of this invention to provide a novel IL-1 production inhibitor which inhibits an abnormal production of IL-1 and enables the institution of judicious therapies in various diseases arising from such abnormal IL-1 production.

With the above objects in mind, the inventor of this invention did much research and, as a consequence, discovered that a carbostyril derivative of the following general formula (1), inclusive of a salt thereof, which was originally developed as an active cardiotonic substance, has a graft rejection inhibitory effect and a graft survival prolonging effect, thus meeting the abovementioned objects. The inventor further discovered that the above compound is an effective IL-1 production inhibitor which expresses its efficacy through a new mechanism of action and has perfected this instant invention.

In accordance with this invention, there is provided a graft rejection inhibitor composition comprising a carbostyril derivative of the following general formula (1) and/or a salt thereof as an active ingredient.

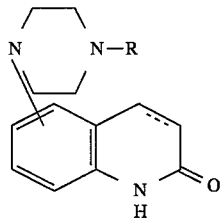

[where R represents a benzoyl group, the phenyl ring of which may optionally be substituted by lower alkoxy, and the bond between 3-carbon and 4-carbon atoms of the carbostyril nucleus represents either a single bond or a double bond.]

In particular, this invention provides said graft rejection inhibitor composition wherein the carbostyril derivative is 6-[4-(3,4-dimethoxybenzoyl)-1-piperazinyl]-3,4-dihydrocarbostyril and/or a salt thereof.

This invention further provides an IL-1 production inhibitor composition comprising a carbostyril derivative of the above general formula (1) and/or a salt thereof as an active ingredient.

In particular, this invention provides said IL-1 production inhibitor composition wherein the carbostyril derivative is 6-[4-(3,4-dimethoxybenzoyl)-1-piperazinyl]-3,4-dihydrocarbostyril and/or a salt thereof.

The graft rejection inhibitor composition of this invention can be indicated with advantage in various transplantations performed in a broad area, including but being not limited to cardiac, pulmonary, hepatic, pancreatic, small intestinal, renal, corneal, dermal, combined heart-lung, and marrow transplantations.

On the other hand, the IL-1 production inhibitor composition of this invention can be applied with advantage to the prevention and treatment of various diseases arising from an abnormal production of IL-1.

The technology for production of the carbostyril derivative of general formula (1), inclusive of a salt thereof, which is used as the active ingredient in the graft rejection inhibitor composition and IL-1 production inhibitor composition of this invention (these compositions are hereinafter referred to collectively as 'the drug of this invention'), is described in inter alia JP Kokoku H1-43747 and it is also known that this carbostyril derivative is of use as a cardiotonic. However, the graft rejection-inhibiting and graft survival-prolonging effect and IL-1 production-inhibiting effect with which this invention is concerned are unrelated to the cardiotonic action and, for that matter, beyond speculation from the cardiotonic action.

The groups shown in the above general formula (1) representing the active ingredient of the drug of this invention respectively include the following.

The lower alkoxy group typically includes straight- or branched-chain alkoxy groups of 1–6 carbon atoms, such as methoxy, ethoxy, propoxy, isopropoxy, butoxy, tert-butoxy, pentyloxy, hexyloxy, etc.

The benzoyl group, the phenyl ring of which may optionally be substituted by lower alkoxy is a benzoyl group optionally having 1–3 straight- or branched-chain alkoxy groups of 1–6 carbon atoms on the phenyl ring, thus including benzoyl, 2-methoxybenzoyl, 3-methoxybenzoyl, 4-methoxybenzoyl, 2-ethoxybenzoyl, 3-ethoxybenzoyl, 4-ethoxybenzoyl, 3-isopropoxybenzoyl, 4-butoxybenzoyl, 2-pentyloxybenzoyl, 3-hexyloxybenzoyl, 3,4-dimethoxybenzoyl, 2,5-dimethoxybenzoyl, and 3,4,5-trimethoxybenzoyl, among others.

The salt of the above carbostyril derivative of general formula (1) includes pharmacologically acceptable acid addition salts. The acidic compound forming the salt includes inorganic acids such as sulfuric acid, phosphoric acid, nitric acid, hydrochloric acid, hydrobromic acid, etc. and organic acids such as oxalic acid, maleic acid, fumaric acid, malic acid, tartaric acid, citric acid, benzoic acid, and so on.

The carbostyril derivative of general formula (1) and/or its salt for use as the active ingredient of the drug of this invention can be supplied generally in conventional pharmaceutical dosage forms. Such dosage forms can be manufactured using the conventional carriers and excipients, such as various fillers, diluents, binders, humectants, disintegrators, surfactants, lubricants, and so on. A suitable pharmaceutical dosage form can be selected according to the therapeutic objective. Thus, tablets, pills, powders, solutions, suspensions, emulsions, granules, capsules, suppositories, injections (injectable solutions, suspensions, etc.), eyedrops, etc. can be mentioned as examples.

For the manufacture of tablets, a broad variety of carriers known in the art can be employed. Thus, excipients such as lactose, sucrose, sodium chloride, glucose, urea, starch, calcium carbonate, kaolin, crystalline cellulose, silica, etc.; binders such as water, ethanol, propanol, simple syrup, glucose syrup, starch solution, gelatin solution, carboxymethyl cellulose, shellac, methylcellulose, potassium phosphate, polyvinylpyrrolidone, etc.; disintegrators such as dried starch, sodium alginate, agar powder, laminaran powder, sodium hydrogen carbonate, calcium carbonate, polyoxyethylene-sorbitan fatty acid esters, sodium lauryl sulfate, stearyl monoglyceride, starch, lactose, etc.; disintegration inhibitors such as sucrose, stearin, cacao butter, hydrogenated oil, etc.; absorption promoters such as quaternary ammonium bases, sodium lauryl sulfate, etc.; humectants such as glycerin, starch, etc.; adsorbents such as starch, lactose, kaolin, bentonite, colloidal silica, etc.; and lubricants such as purified talc, salts of stearic acid, boric acid powder, polyethylene glycol, etc. can be mentioned by way of example. Furthermore, where necessary, tablets may be coated with the conventional coating compositions to provide dragees, gelatin-coated tablets, enteric-coated tablets, film-coated tablets, double-layer tablets, multi-layer tablets and so on.

The manufacture of pills can be carried out using a variety of known carriers, among which various excipients such as glucose, lactose, starch, cacao butter, hydrogenated vegetable oil, kaolin, talc, etc.; binders such as arabic gum powder, tragacanth gum powder, gelatin, ethanol, etc.; and disintegrators such as laminaran and agar can be typically selected.

The manufacture of suppositories can be carried out using a variety of carriers known in the art, such as polyethylene glycol, cacao butter, higher alcohols, higher alcohol esters, gelatin, semi-synthetic glycerides and so on.

In the manufacture of injections, a solution or a suspension is sterilized and preferably isotonized to blood. For the preparation of a solution, emulsion or suspension, any of the diluents in common use in the art can be employed. Thus, for example, water, ethanol, propylene glycol, ethoxylated isostearyl alcohol, polyoxylated isostearyl alcohol, and polyoxyethylenesorbitan fatty acid esters can be utilized. In this procedure, sodium chloride, glucose, glycerin or the like can be added to the composition in an amount sufficient to provide an isotonic preparation. The conventional solubilizers, buffers, soothing agents, etc. may also be incorporated in the pharmaceutical composition. Moreover, where necessary, coloring agents, preservatives, perfumes, flavorants, sweeteners, etc. as well as other medicinal ingredients may be added to the composition.

The proportion of the active ingredient compound of general formula (1) in the drug of this invention is not so critical and can be liberally selected from a broad range. It is, however, recommended that the drug should contain the compound in a proportion of about 1–70% by weight, preferably about 1–30% by weight, relative to the whole composition.

The therapeutic regimen using such a pharmaceutical composition is not so critical and can be chosen according to the dosage form, patient factors such as age and sex, severity of disease, etc. The pharmaceutical composition which is injectable can be administered intravenously, intramuscularly, subcutaneously, intradermally, intraperitoneally or by the like route. Where necessary, the composition can be mixed with the conventional infusion fluid, such as a glucose, amino acid or other intravenous infusion, and administered intravenously. The pharmaceutical composition of this invention in the solid form, e.g. tablets, pills, granules and capsules, or in the peroral liquid form can be administered orally or enterally. The suppositories can be administered into the rectum. The eyedrops can be instilled in the eye.

The dosage of the drug of this invention can be judiciously selected from a broad range and is not so critical. However, in general clinical applications, the daily dose in terms of the carbostyril derivative of general formula (1) (and its salt) is preferably selected from the range of about 0.5 mg to about 30 mg per kg body weight and it is also recommended that, in any of said dosage forms, this active ingredient should occur in a quantity of about 1–1000 mg. Furthermore, the drug of this invention can be administered in a single dose or in 3–4 divided doses daily.

The graft rejection inhibitor composition of this invention or the active ingredient compound therein can be used in combination with the hitherto-known immunosuppressants and the like. In such cases, the active ingredient compound or the graft rejection inhibitor composition of this invention synergistically augments the effects of said concomitant immunosuppressant and other drugs. Therefore, the expected therapeutic responses may be obtained even when the dosage of the concomitant immunosuppressive agent is considerably reduced, thus resulting in the alleviation of unwanted side effects of the concomitant drug.

This invention, thus, provides a graft rejection inhibitor composition comprising a carbostyril derivative of general formula (1) and/or a salt thereof as an active ingredient, which displays a remarkable inhibitory effect on the host's rejection reaction to grafts and enhances the survival rate of the transplanted organs or other tissues.

This invention further provides an IL-1 production inhibitor composition comprising said carbostyril derivative and/or salt as an active ingredient.

BEST MODE OF CARRYING OUT THE INVENTION

Figure 1:
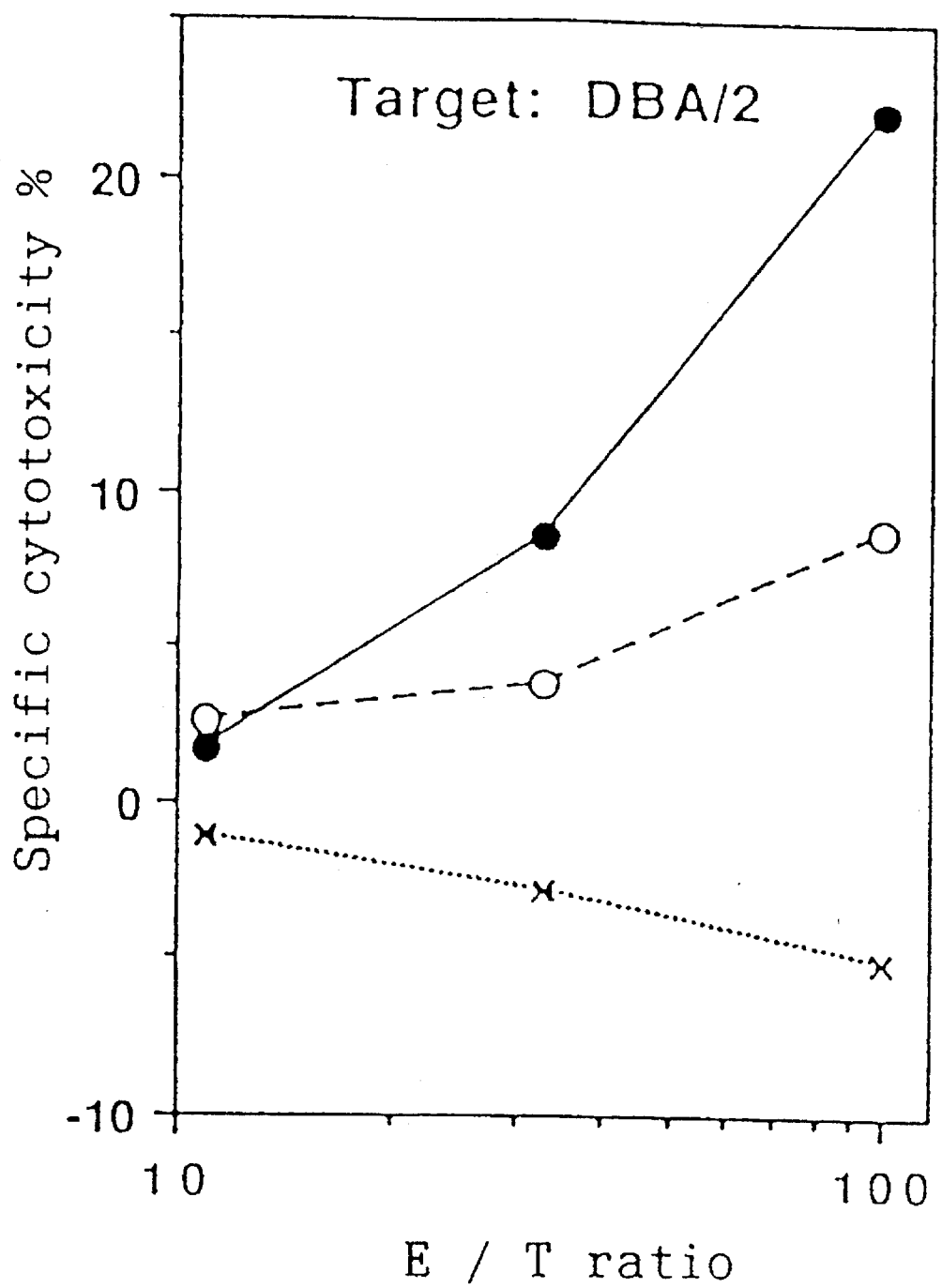
FIGS. 1 and 2 are graphs showing the inhibitory effect of the active ingredient compound of this invention on the induction of cytotoxic T-cells in Pharmacological Test Example 2.

The following formulation examples and pharmacological test examples are intended to describe this invention in further detail. Formulation Example 1

| | |
|---|---|
| 6-[4-(3,4-Dimethoxybenzoyl)-1-piperazinyl]-3,4-dihydrocarbostyril | 5 mg |
| Starch | 132 mg |
| Magnesium stearate | 18 mg |
| Lactose | 45 mg |
| Total | 200 mg |

Tablets of the above formulation per tablet were manufactured.

Formulation Example 2

| | |
|---|---|
| 6-[4-(3,4-Dimethoxybenzoyl)-1-piperazinyl]-3,4-dihydrocarbostyril | 150 g |
| Avicel (tradename, manufactured by Asahi Chemical Industry Co. Ltd.) | 40 g |
| Corn starch | 30 g |
| Magnesium stearate | 2 g |
| Hydroxypropylmethylcellulose | 10 g |
| Polyethylene glycol-6000 | 3 g |
| Castor oil | 40 g |
| Methanol | 40 g |

The above active ingredient compound, Avicel, corn starch and magnesium stearate are mixed, ground, and compressed with a Dragee R10 mm punch. The tablets obtained are coated with a film coating composed of hydroxypropylmethylcellulose, polyethylene glycol-6000, castor oil and methanol to provide film-coated tablets.

Formulation Example 3

| | |
|---|---|
| 6-[4-(3,4-Dimethoxybenzoyl)-1-piperazinyl]-3,4-dihydrocarbostyril | 150.0 g |
| Citric acid | 1.0 g |
| Lactose | 33.5 g |
| Dicalcium phosphate | 70.0 g |
| Pluronic F-68 | 30.0 g |
| Sodium lauryl sulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dried sodium lauryl sulfate | 3.0 g |
| Dried magnesium stearate | 3.0 g |
| Ethanol | q.s. |

The above active ingredient compound, citric acid, lactose, dicalcium phosphate, Pluronic F-68 and sodium lauryl sulfate are admixed.

The above mixture is sieved through a No. 60 screen and wet-granulated with an alcoholic solution containing polyvinylpyrrolidone, Carbowax 1500 and Carbowax 6000. Where necessary, alcohol is added to the granulation to make a paste-like mass. To this mass is added corn starch and the mixing is continued until uniform particles are formed. The mixture is passed through a No. 10 screen, put in a tray and dried in an oven at 100° C. for 12–14 hours. The dried particles are subjected to size selection with a No. 16 screen. Then, dried sodium lauryl sulfate and dried magnesium stearate are added and the mixture is compressed into the desired shape using a tablet machine.

The tablet cores thus obtained are varnished and dusted with talc for preventing absorption of moisture. An undercoating is then applied. The tablets are further varnished in a sufficient number of times to make them suitable for oral ingestion. To insure the true roundness and a smooth surface, further undercoating and smooth coating are applied to the tablets. Then, a color-containing coating is applied until the desired shade is obtained. After drying, the coated tablets are polished to provide finished tablets with a uniform gloss.

Pharmacological Test Example 1

Using 6-[4-(3,4-dimethoxybenzoyl)-1-piperazinyl]-3,4-dihydrocarbostyril (hereinafter referred to Compound 1) as the test compound, the graft rejection-inhibiting effect and graft survival-prolonging effect of the test compound in mouse heterotopic heart transplantation were investigated as follows.

Heterotopic heart transplantation was performed between inbred strain mice and it was investigated whether the survival time of the allografted heart would be extended by the test compound of this invention.

As the donor, DBA/2 mice (6 weeks old, male, purchased from Shimizu Experimental Materials Co., Ltd.) and, as the recipient, C57BL/6 mice (6 weeks old, male, purchased from the above firm) were used.

The heart allografting was carried out by anastomosing the aorta and pulmonary artery of the donor heart to the recipient's abdominal aorta and inferior vena cava, respectively. Postoperatively the viability of the graft was confirmed by palpitation and ECG and the recipient was sacrificed at cardiac arrest.

Compound 1, the test compound, was suspended in 0.5% carboxymethylcellulose (CMC, Cellogen) and this solution was administered orally to the recipient at the dose of 50 mg/kg/day in terms of the test compound once daily beginning the day of operation. The Compound 1 treatment group consisted of 3 mice. A control group, not treated with Compound 1, comprised 7 mice.

The results of the above test showed that with regard to the viability of the transplanted heart in the control group (n=12), cessation of the heartbeat occurred in all cases up to day 12, suggesting rejection of the grafts. In contrast, the heartbeat was still noticeable. in 50% of cases on day 21 in the Compound 1 treatment group (n=10), indicating a remarkable prolongation of graft survival and, hence, a significant inhibition of graft rejection.

It is apparent from the above results that the active ingredient compound of this invention remarkably inhibits graft rejection and enhance the survival rate of transplanted organs.

Pharmacological Test Example 2

The culture and assay of cytotoxic T-lymphocytes were performed as follows.

The mouse spleen was resected and teased to prepare a suspension of discrete cells. After erythrocytes were lysed with ACK lysing buffer (0.15 M $NH_4Cl$, 1.0 M $KHCO_3$, 0.1 mM $Na_2EDTA$, pH 7.4), the suspension was centrifuged (25° C., 20 min., 1500×g) on high-density lympholyte (Cedarlane, Hornby, Ontario, Canada) to recover lymphocytes.

In bulk culture, $7\times10^6$ cells of Mitomycin (25 µg/ml, Sigma, Saint Louis, Mo.)-treated splenic C57BL/6 responder cells (recipient strain) were coincubated, for 5 days, with $5.5\times10^6$ cells of DBA/2 stimulator cells to cause expression of cytotoxic effector cells. To the cytotoxic effector cells were added either $^{51}$Cr-labeled DBA/2 splenic target cells (donor strain) or C3H/He target cells (third party) and the results were recorded. Incidentally, the above two kinds of cells had been preliminarily stimulated with 10 µg/ml of lipopolysaccharide (Difco, Detroit, Mich.) for 2 days beforehand.

The target cells ($1.7\times10^4$) were coincubated with 200 µl/well of C57BL/6 effector cells in three effector/target cell ratios of 100:1, 33:1, and 11:1, using round-bottom 96-well microtiter plates. After 4 hours of incubation in 5% $CO_2$-containing air at 37° C., 100 µl of the supernatant was harvested from each well and its radioactivity was counted using an automatic gamma scintillation counter. The spontaneous $^{51}$Cr release was not more than 30% of the total count.

The specific cytotoxicity was calculated by means of the following equation.

$$\text{Specific cytotoxicity \%} = \frac{\text{(Experimental release cpm-spontaneous release cpm)}}{\text{(Maximum release cpm-spontaneous release cpm)}} \times 100$$

The maximum release cpm mentioned above was determined by treating the $^{51}$Cr-labeled target cells with 0.1% Triton.

In the above test, Compound 1 as the active ingredient compound of this invention was added to the medium at the level of 10 µg/ml. In the in vitro test, the above compound was dissolved in 1N-HCl and diluted with culture medium and its pH was adjusted with 1N-NaOH.

Figure 2:
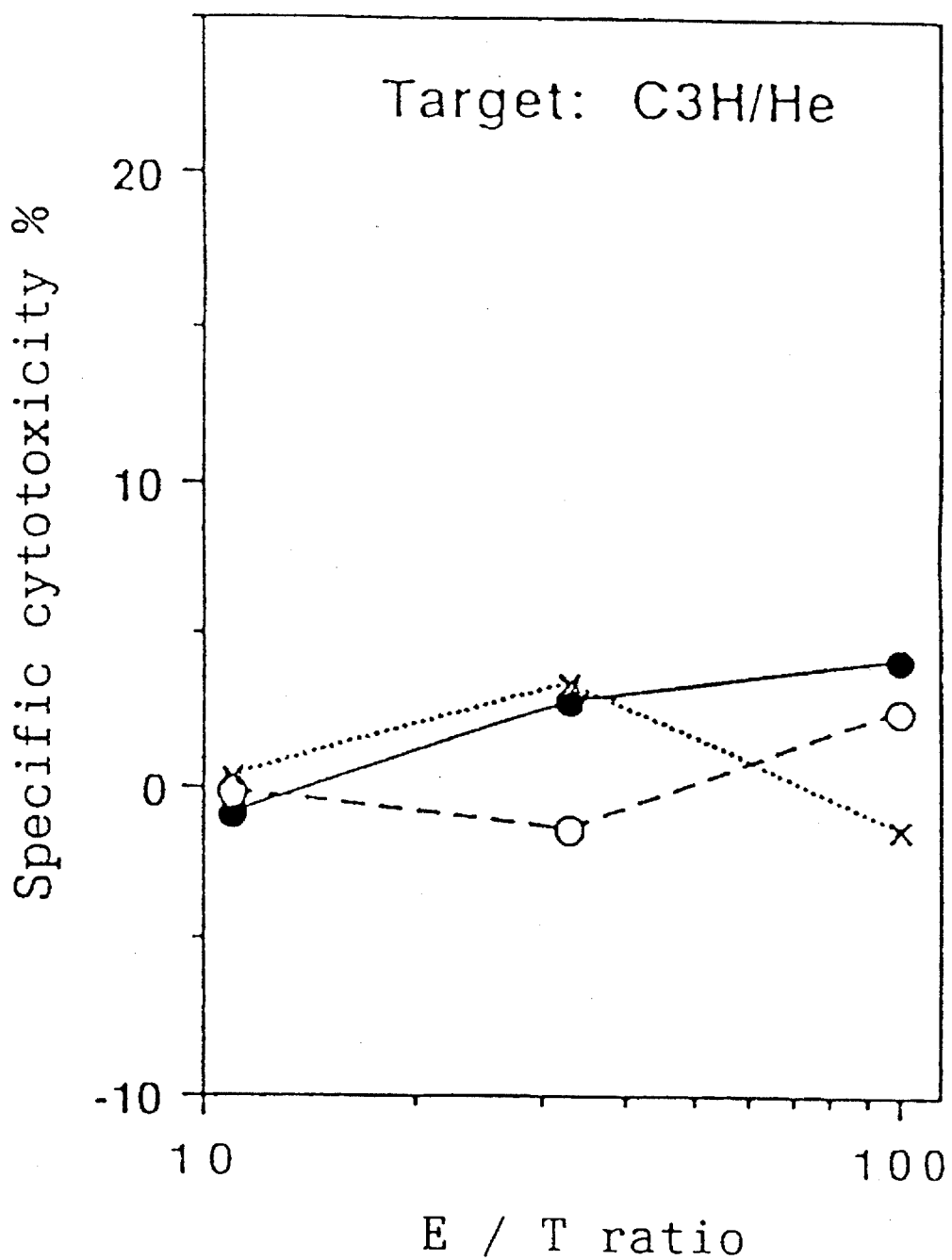

The results are shown in FIGS. 1 and 2.

Each figure is a graph (ordinate: specific cytotoxicity %, abscissa: E/T ratio) showing the inhibitory effect on the appearance of cytotoxic T-cells after treatment in vitro with the active ingredient compound of this invention. Referring to FIG. 1 (DBA/2 cells were used as the target), whereas untreated C57BL/6 splenic cells after reaction with mixed lymphocytes showed an increased CTL for DBA/2 target cells (closed circle), the cells treated with 10 µg/ml of the active ingredient compound of this invention during culture showed a decreased CTL activity (open circle). The mark X represents normal control (C57BL/6 splenic cells not coincubated with DBA/2 target cells).

It is also clear from FIG. 2 (C3H/He cells were used as the target) that when the target is a third party cell line, these C3H/He cells exhibit substantially no cytotoxicity.

Pharmacological Example 3

Human peripheral blood (n=7) was heparinized and 0.5 ml portions thereof were added to 5 ml aliquots of RPMI-1640 medium containing 1, 10, 100, 1000 and 10000 ng/ml of lipopolysaccharide (LPS), respectively. After 24 hours of incubation at 37° C., each culture was centrifuged at 3000 rpm to separate a supernatant and the amounts of IL-1α and IL-1β produced were determined with an ELISA kit (plate solid phase method) using the antibody produced by anti-IL-1α antibody (Hybridoma KOCO 301 (FERM BP 1554) (sensitivity 10 pg/ml, JP Kokai S63-258595) and the antibody produced by anti-IL-1β antibody (Hybridoma GOM 43-4, FERM BP 2565) (sensitivity 20 pg/ml, JP Kokai H2-227094), respectively. The above assays were carried out in accordance with the method described in Iida, M., et. al., Jap. J. Clin. Path. 3.6, 196 (1988) for IL-1α and the method described in Noda, A., et. al., Jap. J. Clin. Path..36, 197 (1988) for IL-1β.

Prior to addition of said LPS, Compound 1 as the test compound was added, as previously suspended in carboxymethylcellulose (CMC solution, Dai-Ichi Kogyo Seiyaku Co., Ltd.), to each sample at a final concentration of 10 μg/ml (experimental group). A Compound 1-free control group was also provided.

Figure 3:
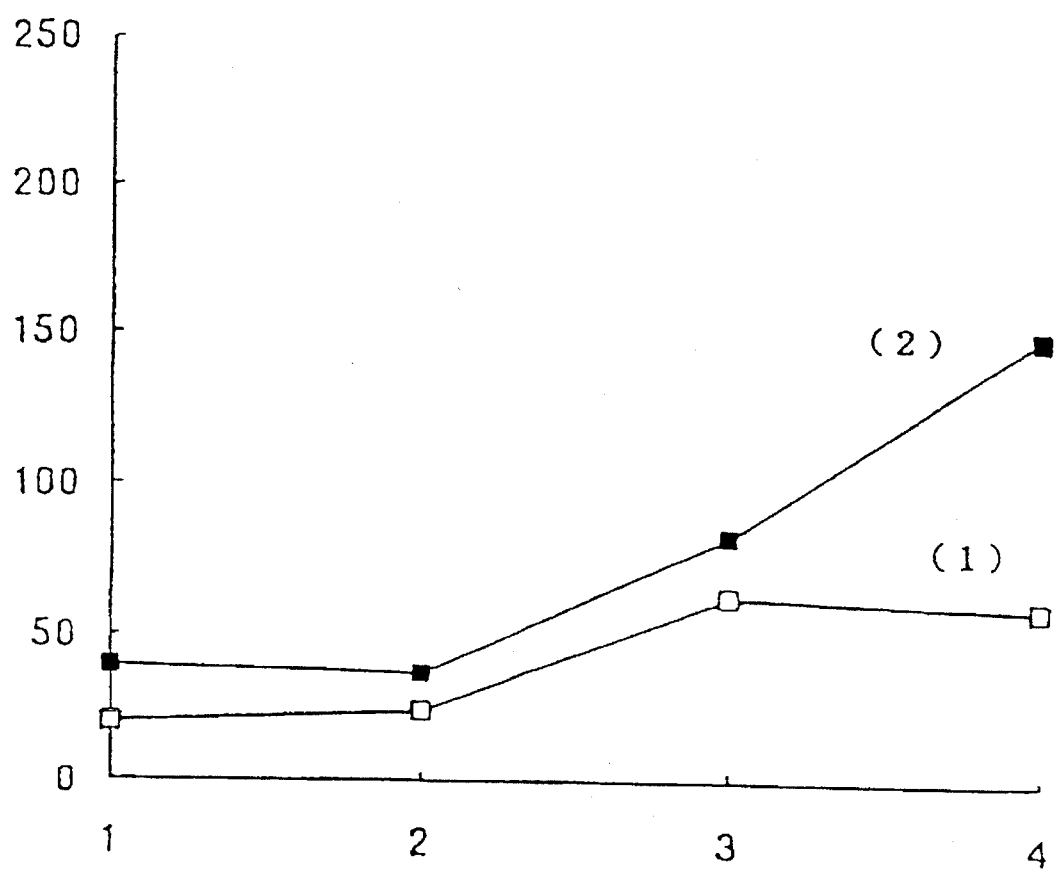
FIG. 3 is a graph showing the IL-1α production inhibiting activity of the active ingredient compound of this invention in Pharmacological Test Example 3.
Figure 4:
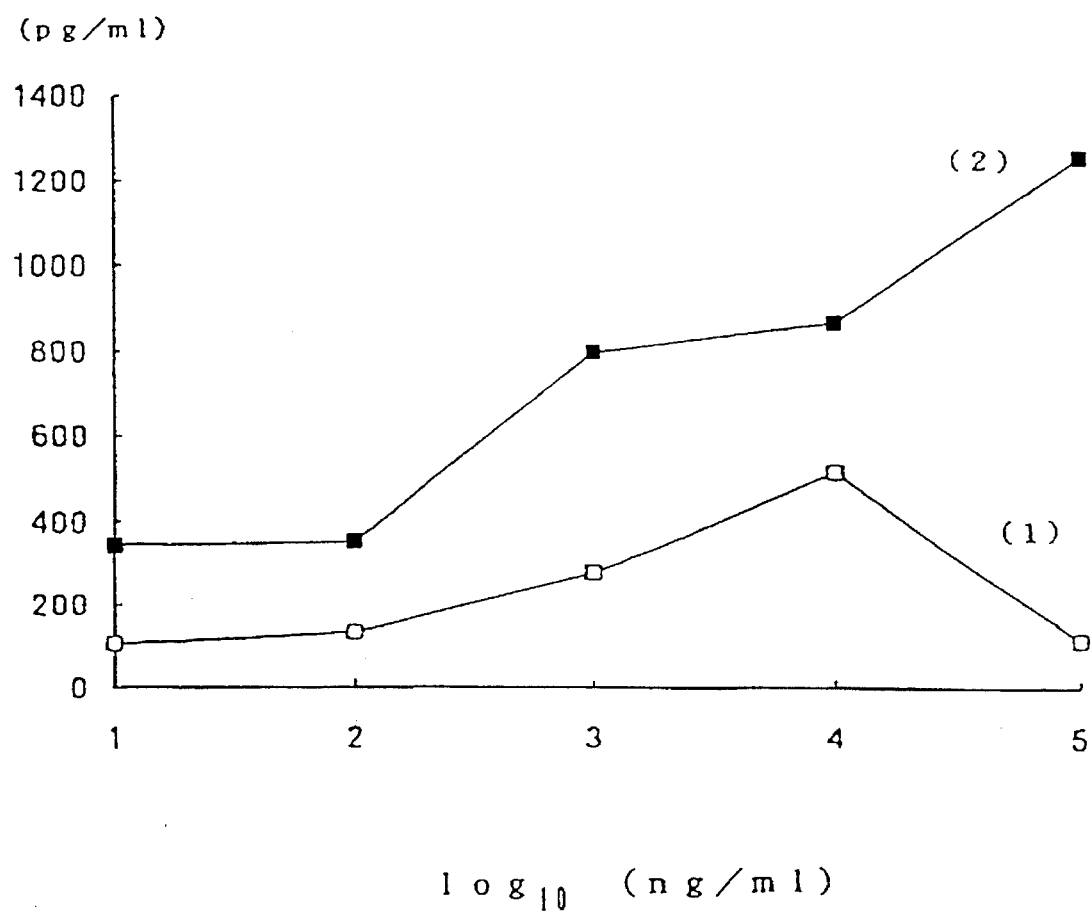
FIG. 4 is a graph showing the IL-1β production-inhibiting activity of the active ingredient compound of this invention in Pharmacological Test Example 3.

The assay results in the above experimental group and those in the control group are shown for comparison in FIGS. 3 and 4.

FIG. 3 is a graph showing the amounts of IL-1α produced in the experimental group and control group, wherein the ordinate represents the output of IL-1α (pg/ml) and the abscissa represents the concentration of LPS added (expressed on log scale). In the graph, (1) represents the experimental group and (2) represents the control group.

It is apparent from the graph that the active ingredient compound of this invention significantly inhibits the LPS-stimulated production of IL-1α in peripheral blood.

FIG. 4 is a graph showing the amounts of IL-1β produced in the experimental group and control group, wherein the ordinate represents the output of IL-1β (pg/ml) and the abscissa represents the concentration of LPS added (expressed on log scale). In the graph, (1) represents the experimental group and (2) represents the control group.

It is apparent from this graph that the active ingredient compound of this invention significantly inhibits the LPS-stimulated production of IL-1β in peripheral blood.

Thus, the active ingredient compound of this invention is capable of inhibiting IL-1 production, indicating that it is useful for the therapy of various inflammatory diseases and for antipyresis, increase of appetite, and inhibition of slow-wave sleep.

Pharmacological Test Example 4

In the postoperative immunotherapy following a cardiac or other organ transplantation, cyclosporine A (Cy-A) is playing a central role but complications of the therapy, such as renal failure, are serious problems. It is known that these complications are dependent on the dosage of Cy-A. Therefore, it is of significance to reduce the dosage of Cy-A.

In this test, the drug (Compound 1) of this invention was administered in combination with Cy-A to investigate the allograft survival-prolonging effect of the combination therapy.

Using 7–10-week-old C57BL/6 mice (male) as the recipient and DBA/2 mice (male) as the donor, the donor heart was allografted into the recipient's abdominal cavity. Beginning the day of transplantation, the test drug was administered orally via a stomach tube once daily or every 24 hours. The recipient mice were monitored for rejection of the allografted heart by daily palpitation and by ECG recording made 3 times a week and final assessments were made based on histological findings.

First, Cy-A alone was administered and the maximum dose that did not significantly prolong the allograft survival compared with no administration (control) was determined.

Then, among the group receiving the above maximum dose (20 mg/kg/day) (Cy-A monotherapy group), the group receiving 10 mg/kg/day of the drug of this invention alone (Compound 1 monotherapy group), and the group receiving the same doses of both drugs (Cy-A+Compound 1 combination therapy group), the graft survival-prolonging effect was compared.

Figure 5:
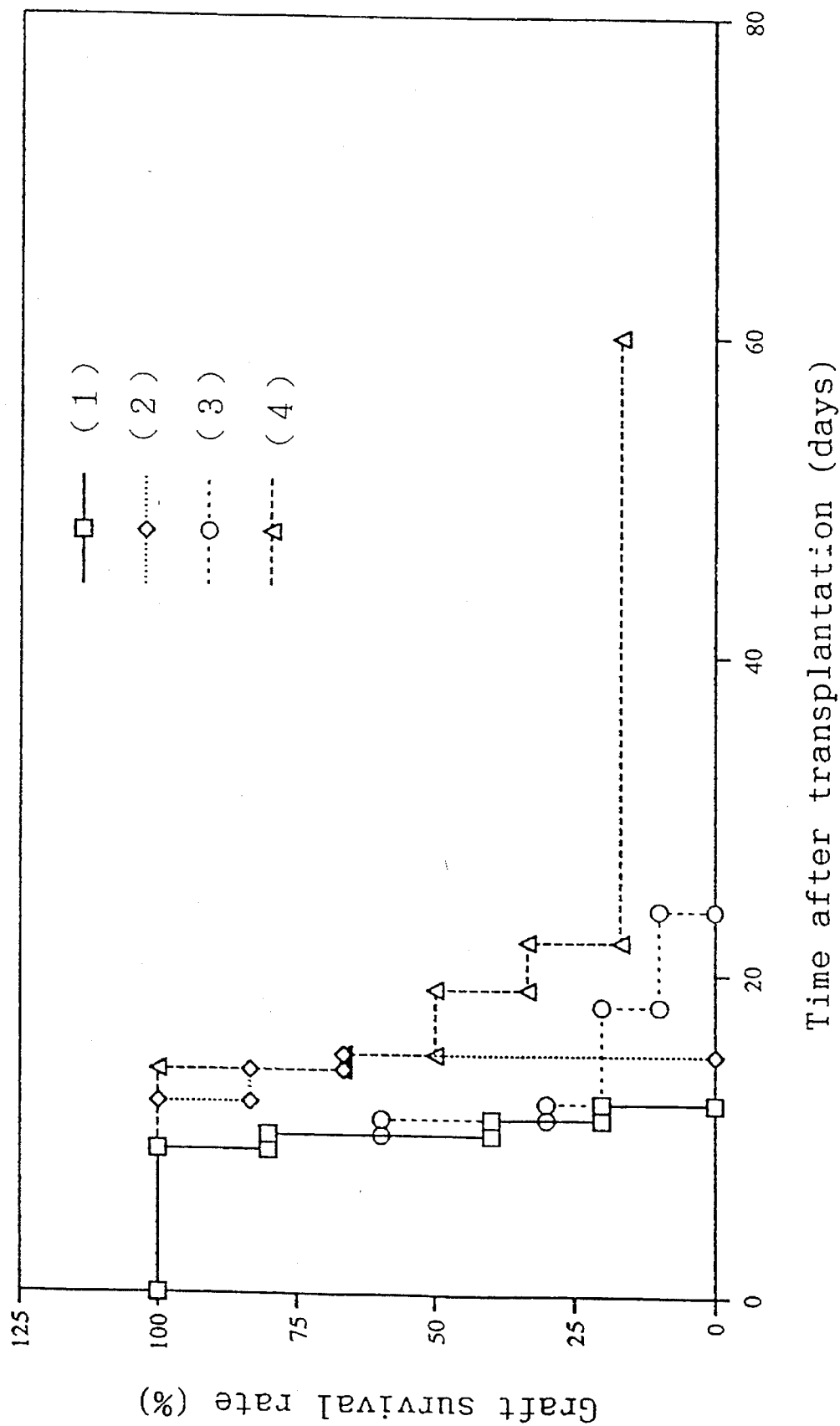
FIG. 5 is a graph showing the graft rejection-inhibiting effect of the active ingredient compound of this invention in Pharmacological Test Example 4.

The results are shown in FIG. 5.

In the graph, the abscissa represents the time (in days) after transplantation and the ordinate represents the graft survival rate (%). Further, (1) represents the control group (no drug was administered, n=10), (2) represents the Cy-A monotherapy group (n=6), (3) represents the Compound 1 monotherapy group (n=10), and (4) represents the Cy-A+Compound 1 combination therapy group (n=6).

It is apparent from this graph that compared with the monotherapy groups (2) and (3), the Cy-A+Compound 1 combination group (4) showed a prolongation of graft survival.

I claim:

1. A method of inhibiting graft rejection in a subject in need of such inhibition comprising administering to said subject a pharmaceutically effective amount of a carbostyril derivative of the following formula (1), and/or a salt thereof:

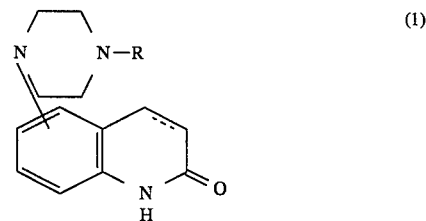

wherein R represents a benzoyl group, the phenyl ring of which may optionally be substituted by a lower alkoxy group, and the bond between the 3-carbon and 4-carbon atoms of the carbostyril nucleus represents either a single bond or a double bond.

2. The method according to claim 1, wherein said carbostyril derivative is 6-[4-(3,4-dimethoxybenzoyl)-1-piperazinyl]-3,4-dihydrocarbostyril.

3. A method of inhibiting IL-1 production in a subject in need of such inhibition comprising administering to said subject a pharmaceutically effective amount of a carbostyril derivative of the following formula (1), and/or a salt thereof:

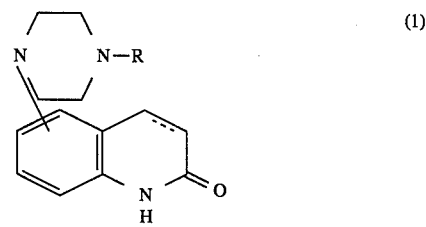

wherein R represents a benzoyl group, the phenyl ring of which may optionally be substituted by a lower alkoxy group, and the bond between the 3-carbon and 4-carbon atoms of the carbostyril nucleus represents either a single bond or a double bond.

4. The method according to claim 3 wherein said carbostyril derivative is 6-[4-(3,4-dimethoxybenzoyl)-1-piperazinyl]-3,4-dihydrocarbostyril.

* * * * *

UNITED STATES PATENT AND TRADEMARK OFFICE
CERTIFICATE OF CORRECTION

PATENT NO. : 5,521,185
DATED : May 28, 1996
INVENTOR(S) : Akira Matsumori

It is certified that error appears in the above-indentified patent and that said Letters Patent is hereby corrected as shown below:

On title page, item [87], change "WO 94/21836" to -- WO 94/20107 --.

On the Cover Page, change "September 29, 1994" to -- September 15, 1994 --.

On title page, item [30], change "Mar. 2, 1993 [JP] Japan .......... 5-041227" to -- Mar. 2, 1993 [JP] Japan ....... 5-41115 --.

Signed and Sealed this

Tenth Day of September, 1996

Attest:

BRUCE LEHMAN

*Attesting Officer*  *Commissioner of Patents and Trademarks*